United States Patent [19]
Lasser et al.

[11] Patent Number: 5,793,791
[45] Date of Patent: Aug. 11, 1998

[54] LASER ARRANGEMENT AND METHOD OF OPERATING SAID LASER ARRANGEMENT

[75] Inventors: Theo Lasser, Oberkochen; Robert Maag, Aalen; Heinz Abramowsky, Giengen; Martin Wiechmann, Jena, all of Germany

[73] Assignee: Carl-Zeiss-Stiftung, Heidenheim, Germany

[21] Appl. No.: 594,438

[22] Filed: Jan. 31, 1996

[30] Foreign Application Priority Data

Jan. 31, 1995 [DE] Germany ............... 195 02 931.3

[51] Int. Cl.$^6$ ............................................. H01S 3/09
[52] U.S. Cl. ........................... 372/69; 372/6; 372/22
[58] Field of Search ........................ 372/69–72, 92, 372/29, 75, 6, 22

[56] References Cited

U.S. PATENT DOCUMENTS

| | | | |
|---|---|---|---|
| 4,791,631 | 12/1988 | Baumert et al. | 372/75 |
| 4,794,615 | 12/1988 | Berger et al. | 372/69 |
| 4,977,561 | 12/1990 | Ibe et al. | 372/29 |
| 5,214,666 | 5/1993 | Watanabe et al. | 372/69 |
| 5,272,713 | 12/1993 | Sobey et al. | 372/69 |

*Primary Examiner*—Leon Scott, Jr.
*Attorney, Agent, or Firm*—Walter Ottesen

[57] ABSTRACT

At least one narrow-band emitting pump radiation source is provided in a laser arrangement having a laser medium to be pumped. The supplied pump radiation includes at least two pump radiation components which are different with respect to power. The component with lower power functions to generate a visible target beam. Such a laser arrangement is especially suitable in a medical laser system.

9 Claims, 1 Drawing Sheet

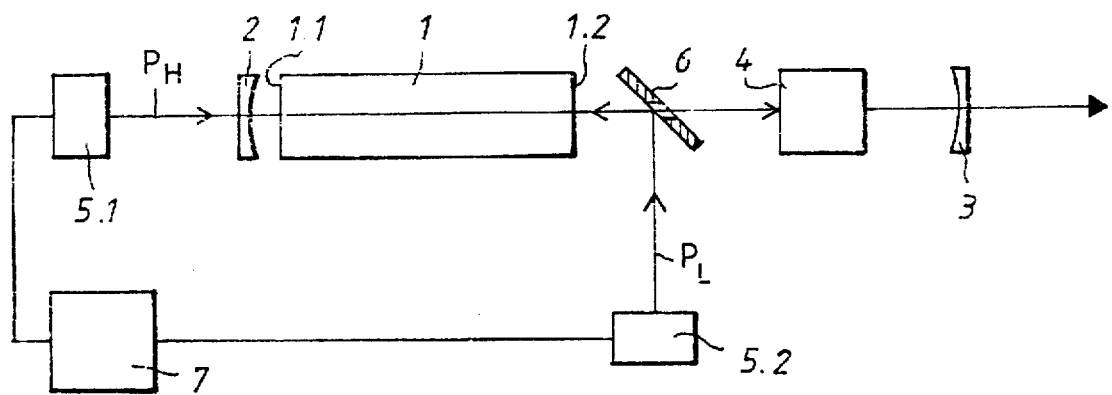
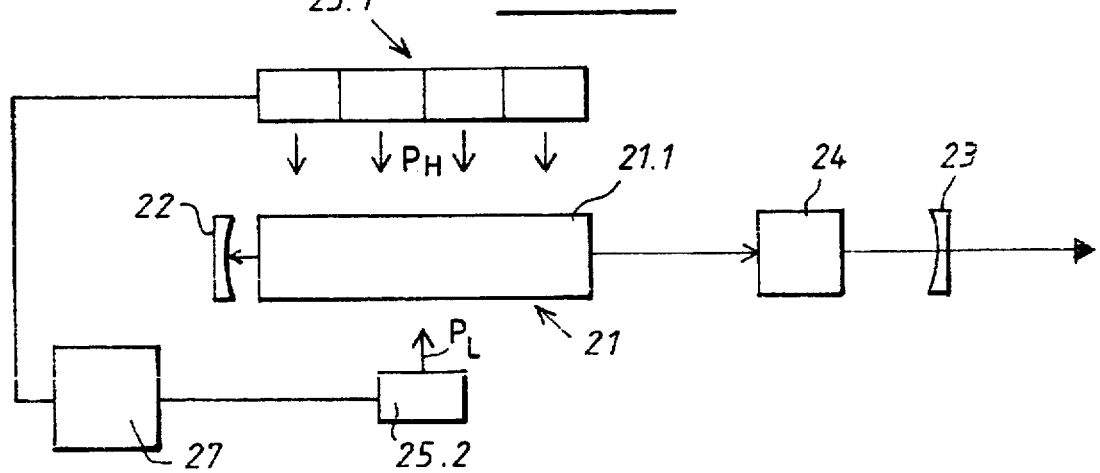
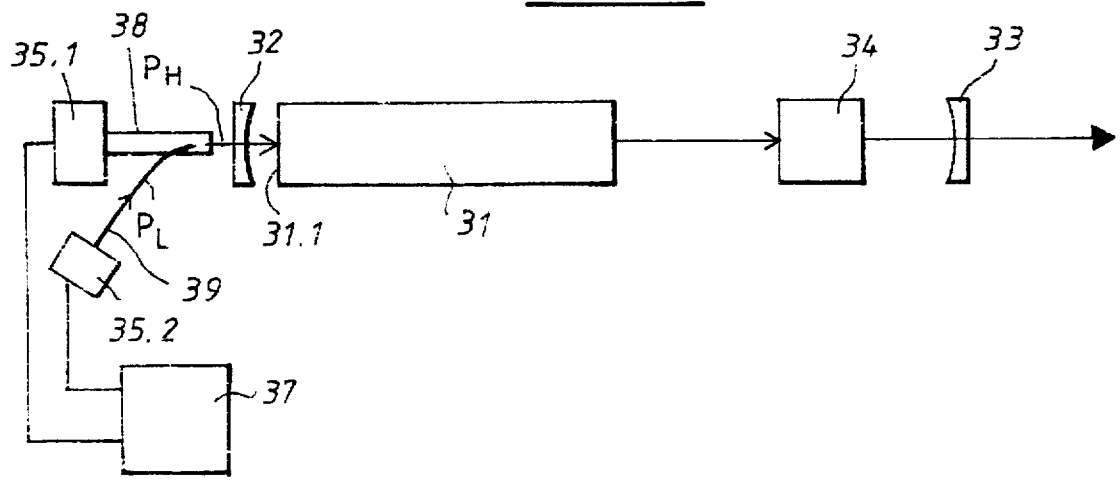

LASER ARRANGEMENT AND METHOD OF OPERATING SAID LASER ARRANGEMENT

FIELD OF THE INVENTION

The invention relates to a laser arrangement having a laser medium to be pumped as well as at least one narrow-band emitting pump radiation source. A method for operating such a laser arrangement is also the subject matter of the invention. The laser arrangement according to the invention as well as the method of the invention are especially suitable for a medical laser.

BACKGROUND OF THE INVENTION

In the medical area, lasers are used for various applications to an increasing extent. The medical lasers known up to now supply a work or therapeutical beam of higher energy which causes, in dependence upon wavelength, specific interactions with the tissue to be treated. Furthermore, a so-called target laser is usually provided in a laser arrangement of this kind to enable the operating surgeon to precisely determine the desired target in advance of using the actual work beam. The most varied combinations and generating possibilities for the work and target beams are known. Accordingly, it is possible to use an invisible work beam having a wavelength of 1.064 μm emitted by a Nd:YAG laser in combination with a visible target beam in the red spectral range. The target beam is, in turn, generated by a separate helium neon laser of low power.

In contrast, for ophthalmology, mostly laser wavelengths which lie in the green spectral range are required for a series of applications. Argon-ion lasers are mostly used for this purpose. It is also known to use frequency-doubled Nd:YAG lasers in this spectral range.

The required target beam is generated in laser systems of this kind either by a separate helium neon laser or by a laser diode and, in each case, in the red spectral range and with low power. However, the red target beam is not optimal for the treating physician because of the absorption and reflection characteristics of the retina. Instead, a green target beam having low power would be better suited. A green target beam can, for example, be generated by attenuating the green work beam which however is associated with a considerable loss of power of the laser arrangement utilized. In contrast, the use of a separate laser for generating a target beam is complex.

SUMMARY OF THE INVENTION

In view of the foregoing, it is an object of the invention to provide a laser arrangement as well as a method for operating the same which avoids the disadvantages of the state of the art. It is another object of the invention to provide an efficient, low loss and reliable generation of a target beam in a laser arrangement.

The laser arrangement of the invention includes: a laser medium; at least one narrow-band emitting pump radiation source for supplying pump radiation including at least a first pump radiation component of a first power ($P_L$) and a second pump radiation component of a second power ($P_H$) different from the first power; and, a device for operating on the pump radiation source to selectively activate the first and second pump radiation components to optically pump the laser medium.

According to the invention, the particular laser medium is itself directly utilized also for generating a visible target beam in harmless power ranges. For this purpose, a narrow-band emitting pump radiation source is selected where supplies at least two pump radiation components which are different with respect to power. This pump radiation source is suitable for a defined excitation of specific laser wavelengths of the laser medium. The pump radiation components are different with respect to power and can be selectively activated.

Alternatively, two or more pump radiation sources can be utilized which supply the pump radiation components of different power. The desired target beam is generated by the pump radiation of relatively low pump power; whereas, the actual work beam is generated by the other pump radiation component which is of significantly greater power. This ensures that the target beam, which is generated by pump radiation of low power, cannot exceed a specific power limit and therefore cannot have any damaging effects.

Both the laser arrangement and method of the invention are suitable for different known pump geometries.

The most different laser media can be used, that is, laser media which inherently supply visible laser radiation or laser media which can generate laser radiation in the visible spectral range by means of known frequency-doubling materials.

An efficient total system with respect to energy and having a low power loss is provided with the laser arrangement and method according to the invention. Here, the generation of the desired target beam is associated only with a low resulting power loss. This means, in turn, that the development of heat which otherwise results because of a high power loss during target beam operation can be avoided.

In addition to the mentioned application in medical laser systems, the laser arrangement of the invention can also be used in known laser material processing apparatus wherein visible target radiation is also required.

BRIEF DESCRIPTION OF THE DRAWINGS

Further advantages as well as details of both the laser arrangement and the method of the invention will become evident from the following description of the embodiments with reference to the enclosed figures wherein:

FIG. 1 is a schematic block diagram of a laser arrangement according to a first embodiment of the invention wherein the pump radiation components are supplied to the laser medium from two pump radiation sources via the longitudinal end faces thereof;

FIG. 2 is a schematic block diagram of a laser arrangement according to a second embodiment of the invention wherein the pump radiation sources are arranged transversely of the laser medium; and, FIG. 3 is a schematic block diagram of a laser arrangement according to a third embodiment of the invention wherein the laser medium is pumped via a fiber bundle.

DESCRIPTION OF THE PREFERRED EMBODIMENTS OF THE INVENTION

In FIG. 1, a solid state material in the form of a rod-shaped Nd-doped YAG crystal 1 is provided as a laser medium. At an appropriate excitation, the YAG-crystal 1 supplies a laser wavelength of 1.064 μm in the infrared spectral range. As an alternative to the known host material YAG (Yttrium-aluminum-granate), the use of other host materials such as YLF, YVO$_4$, YAP or GGG is however also possible. These host materials can each be doped with Nd ions. Furthermore, the use of a Yb:YAG crystal as suitable solid-state laser medium would also be possible.

The rod-shaped Nd:YAG crystal 1 is mounted within a resonator in a manner known per se. The resonator is defined by the two delimiting resonator mirrors (2, 3). In the resonator, a frequency multiplier element 4 is mounted between the rod-shaped Nd:YAG crystal 1 and the out-coupling mirror 3. For this purpose, an optically nonlinear crystal is preferably used which serves to multiply the frequency of the fundamental wavelength supplied by the laser medium. As suitable crystal materials, KTP crystals as well as LBO crystals can be considered which, in each case, effect a frequency doubling of the fundamental wavelength.

Furthermore, several such frequency multiplier elements can be provided in the resonator in dependence upon the desired application and output wavelength.

In the illustrated embodiment of FIG. 1, the infrared wavelength of 1.064 μm supplied by the Nd:YAG crystal 1 is frequency doubled via the frequency multiplier element 4, that is, the laser arrangement supplies output radiation in the green spectral range at 532 nm. This wavelength is suitable especially for a multiplicity of applications in the ophthalmic area.

In the illustrated embodiment of FIG. 1, two narrow-band emitting pump radiation sources (5.1, 5.2) are provided to optically pump the laser medium, that is, the rod-shaped Nd:YAG-crystal 1. The pump radiation sources (5.1, 5.2) are each mounted outside of the resonator. The rod-shaped Nd:YAG crystal 1 as well as the two pump radiation sources (5.1, 5.2) are mounted in an end face pumped configuration in the illustrated embodiment. The pump radiation ($P_L$, $P_H$) is supplied to the rod-shaped Nd:YAG crystal 1 via the two rod end faces (1.1, 1.2).

As narrow-band emitting pump radiation sources, especially semiconductor lasers such as known GaAs laser diodes, et cetera are especially suitable in an advantageous manner. Depending upon the laser medium to be pumped, the required pump wavelength can be suitably selected in order to ensure a high efficiency of the total system.

The two pump radiation sources (5.1, 5.2) are shown in the illustrated embodiment, each being configured as laser diodes which supply pump radiation ($P_H$, $P_L$) at a wavelength of 807 nm. Both pump radiation sources (5.1, 5.2) supply pump radiation components ($P_H$, $P_L$) which are different with respect to power. Here, the laser diodes of the firm Spectra Diode Labs can, for example, be considered having the type designations SDL 5410 ($P_L$) and SDL 3450-P6 ($P_H$).

As an alternative to the embodiment shown, the two pump radiation components, which are different at least with respect to power, can exhibit different wavelengths by utilizing a laser medium which can emit different laser wavelengths depending upon excitation.

By means of a first pump radiation source 5.1, the laser medium, which is in the form of a rod-shaped Nd:YAG crystal 1, is end pumped through the resonator end mirror 2 in a manner known per se and excited to the desired laser activity. The first pump radiation source 5.1 supplies the higher-power pump radiation component $P_H$ and thereby serves to generate the desired work beam. The use of known laser diode arrays is advantageous for generating a higher-power pump radiation component $P_H$. Such laser diodes are likewise available from Spectra Diode Labs noted above.

A work beam having an output power of approximately 1 W results with a pump radiation power $P_H$ of 15 W. This is adequate for ophthalmic use. The resulting infrared fundamental wavelength of the rod-shaped Nd:YAG crystal 1 is frequency doubled via the frequency multiplier element 4 in the embodiment shown, that is, the resulting infrared fundamental wavelength is converted into green laser radiation having a wavelength of 532 nm and leaves the resonator as a work beam via the out-coupling mirror 3.

The second pump radiation source 5.2 pumps the rod-shaped Nd:YAG crystal 1 longitudinally with a second pump radiation component $P_L$ which is lower with respect to power. The second pump radiation component $P_L$ is supplied via an apertured mirror 6 to the second rod end face 1.2 in the embodiment shown. The apertured mirror 6 is mounted in the resonator. In this way, the pump radiation component $P_L$ is directed in the direction of the rod end face 1.2 via the apertured mirror.

As an alternative to the apertured mirror 6, a suitable dichroic beam splitter element can be mounted in the resonator.

The second pump radiation component $P_L$ exhibits a significantly lower power and therefore supplies only an output beam of lower power. This output beam likewise has a wavelength of 532 nm in the green spectral range because of the frequency multiplying element 4 in the resonator. Accordingly, the output beam functions as a visible target beam of low power. A green target beam having an output power of several mW results when utilizing a laser diode having a pump power of approximately 100 mW.

In target beam operation, the laser arrangement of the invention is accordingly excited via the pump radiation source 5.2 with low pump power and supplies a target beam in the visible spectral range which lies in a harmless power range because of the low pump power. In this connection, it has been shown to be advantageous for safety reasons to select, ab initio, the pump radiation source 5.2 for the target beam operation so that a specific maximum pump power cannot be exceeded, that is, a specific target beam power can also not be exceeded. This ensures that the target beam cannot exceed a defined maximum power even in the case of a possible error when activated by this pump radiation source 5.2.

In contrast, in the actual work beam operation, the pumping of the laser arrangement takes place via the second pump radiation source 5.1 which is designed to provide significantly greater power. There results then the required work beam power for coagulation and the like as initially described.

A control unit 7 has an appropriate control logic and is provided for reliable operation of the laser arrangement of the invention. Depending upon the desired mode of operation (target beam operation or work beam operation), the laser arrangement of the invention selectively activates the required pump radiation source (5.1, 5.2) and thereby also the particular required pump radiation component ($P_L$, $P_H$). The control unit 7 then can be realized, for example, in the form of a computer having corresponding control software.

The embodiment of FIG. 1 has two separate pump beam sources and, in addition to this embodiment, it is possible to provide only a single pump beam source which can supply the required high pump radiation component for the specific area of application. At the same time, this pump radiation source can however also be so operated that a lower-power pump radiation component is generated via this pump radiation source. Accordingly, a corresponding control unit is necessary which causes the single pump radiation source to emit the particular required pump power in dependence upon the desired operation. The control unit then includes a current supply unit for the pump radiation source which can be controlled within corresponding limits. Laser diodes and laser diode arrays are suitable in an advantageous manner as pump radiation sources.

A further embodiment of the laser arrangement of the invention is shown in FIG. 2. In contrast to the embodiment of FIG. 1 first described, the laser medium is no longer pumped via the end faces (that is, longitudinally), instead a transversely arranged pump configuration is used. The laser medium is here too configured as a rod-shaped Nd:YAG crystal 21. The pump radiation reaches the laser medium via the lateral faces (21.1, 21.2) of the rod-shaped Nd:YAG crystal. For this purpose, known pump arrangements having cylinder optics (not shown) for focussing the pump radiation are suitable.

The remaining resonator configuration with the two resonator mirrors (22, 23) as well as the frequency multiplier element 24 is otherwise identical to the embodiment just described.

The pump radiation supplied by the two narrow-band emitting pump radiation sources (25.1, 25.2) is again made up of a pump radiation component $P_H$ of higher power as well as a corresponding pump radiation component $P_L$ of correspondingly lower power. A pump radiation source 25.1 for the pump radiation component of higher power is shown schematically and is in the form of a laser diode array; whereas, for generating the pump radiation of lower power, a laser diode of lower power is utilized.

Furthermore, a control unit 27 is provided which functions as described above.

In addition to the two embodiments of FIGS. 1 and 2 having purely longitudinally or purely transverse pump arrangements for the two pump radiation components, mixed pump arrangements can also be used according to the invention.

Thus, in a further embodiment, the pump radiation component of higher power can excite the laser medium via a transverse pump arrangement according to the embodiment of FIG. 2. In contrast, the pump radiation component of lower power is supplied to the laser medium via a longitudinal pump configuration as described with respect to FIG. 1.

Alternatively, a reverse configuration can be provided.

A third embodiment of the laser arrangement of the invention is shown in FIG. 3. The resonator configuration includes the rod-shaped laser medium in the form of a Nd:YAG crystal 31, the two resonator mirrors (32, 33) as well as the frequency multiplier element 34. This resonator assembly is again basically identical to the embodiments described initially. What is different with respect to the above is that, in this embodiment, the pumping of the rod-shaped Nd:YAG crystal 31 is realized via a fiber bundle 38. The Nd:YAG crystal is pumped at its end 31.1 through the resonator mirror 32 via the outcouple end of the fiber bundle 38. At the incouple end, and forward of the fiber bundle 38, two pump radiation sources (35.1, 35.2) are, in turn, mounted having different pump power components ($P_L$, $P_H$). In the embodiment shown, the largest cross-sectional component of the fiber bundle 38 is utilized for transmitting the pumped radiation of higher power; whereas, a single fiber 39 is used to transmit the relatively low pump power for the viewable target beam. The single fiber 39 is connected to the fiber bundle 38 having a larger cross section.

Otherwise, this embodiment of the laser arrangement according to the invention operates essentially as initially described with respect to the target beam operation and work beam operation and especially a corresponding control unit 37 is provided.

It is understood that the foregoing description is that of the preferred embodiments of the invention and that various changes and modifications may be made thereto without departing from the spirit and scope of the invention as defined in the appended claims.

What is claimed:

1. A laser arrangement for selectively supplying a target beam or a work beam, said laser arrangement comprising:
    a laser medium;
    a first narrow-band emitting pump radiation source supplying pump radiation of a first power to excite said laser medium to supply a work beam of high energy;
    a second narrow-band pump radiation source supplying pump radiation of a second power less than said first power to excite said laser medium to supply a target beam of low energy in a visible spectral range;
    a control unit connected to said first pump radiation source and said second pump radiation source; and,
    said control unit being configured to activate either said first pump radiation source or said second pump radiation source to optically pump said laser medium to output either said work beam of said high energy or said target beam of said low energy in said visible spectral range in dependence upon which one of said work beam or said target beam is desired.

2. The laser arrangement of claim 1, said first pump radiation source being configured to supply pump radiation of a given wavelength and said second pump radiation sources each being configured to also supply pump radiation of said wavelength.

3. The laser arrangement of claim 1, said laser medium having a rod-shaped configuration; and, said first pump radiation source and said second pump radiation source being mounted longitudinally of said laser medium.

4. The laser arrangement of claim 1, said laser medium having a rod-shaped configuration; and, said first pump radiation source and said second pump radiation source being mounted transversely of said laser medium.

5. The laser arrangement of claim 1, said laser medium having a rod-shaped configuration; and, said laser arrangement further comprising:
    a fiber bundle connected to said laser medium;
    said fiber bundle including: a first component connected to said first narrow-band emitting pump radiation source for transmitting said pump radiation of said first power to said laser medium; and, a second component connected to said second narrow-band pump radiation source for transmitting said pump radiation of said second power to said laser medium;
    said first component having a first cross section and said second component having a second cross section; and, said first cross section being greater than said second cross section.

6. The laser arrangement of claim 1, at least one of said first and said second pump radiation sources including a semiconductor laser.

7. The laser arrangement of claim 1, at least one of said first and said second pump radiation sources including a laser-diode array.

8. The laser arrangement of claim 1, said laser medium being a solid state material.

9. The laser arrangement of claim 1, further comprising a laser resonator defining a optical axis and said laser medium being mounted on said axis; and, said laser resonator including a frequency multiplier mounted on said axis.

* * * * *